United States Patent
Higgs

(10) Patent No.: US 10,354,752 B2
(45) Date of Patent: Jul. 16, 2019

(54) UNIVERSAL ACCESS SMART CARD FOR PERSONAL HEALTH RECORDS SYSTEM

(71) Applicant: Robert Higgs, Evansville, IN (US)

(72) Inventor: Robert Higgs, Evansville, IN (US)

( * ) Notice: Subject to any disclaimer, the term of this patent is extended or adjusted under 35 U.S.C. 154(b) by 0 days.

(21) Appl. No.: 14/796,774

(22) Filed: Jul. 10, 2015

(65) Prior Publication Data
US 2017/0011174 A1    Jan. 12, 2017

(51) Int. Cl.
G06F 19/00 (2018.01)
H04L 29/08 (2006.01)
G16H 10/65 (2018.01)
G16H 10/60 (2018.01)

(52) U.S. Cl.
CPC .......... G16H 10/65 (2018.01); G16H 10/60 (2018.01); H04L 67/10 (2013.01)

(58) Field of Classification Search
CPC ...... G06F 19/323; G06F 19/322; G16H 10/65
USPC ........................................ 705/2–4
See application file for complete search history.

(56) References Cited

U.S. PATENT DOCUMENTS

| | | | | |
|---|---|---|---|---|
| 8,380,630 B2 * | 2/2013 | Felsher | ................. | G06F 19/328 705/50 |
| 2002/0147726 A1 * | 10/2002 | Yehia | ..................... | G06Q 10/10 |
| 2003/0217206 A1 * | 11/2003 | Poo | ....................... | G06F 3/0607 710/68 |
| 2005/0080812 A1 * | 4/2005 | Matsumoto | ........... | G06F 17/272 |
| 2006/0173712 A1 * | 8/2006 | Joubert | .................. | G06Q 10/10 705/2 |
| 2007/0016452 A1 * | 1/2007 | Wilson, III | ............ | G16H 10/65 705/3 |
| 2007/0061266 A1 * | 3/2007 | Moore | ................... | G06Q 50/00 705/51 |
| 2007/0226010 A1 * | 9/2007 | Larsen | ................. | G06Q 10/109 705/2 |
| 2008/0059236 A1 * | 3/2008 | Cartier | .................. | G06F 19/323 705/3 |
| 2008/0071577 A1 * | 3/2008 | Highley | ................ | G06F 19/322 705/3 |
| 2013/0197941 A1 * | 8/2013 | Cochran | ............... | G06F 19/322 705/3 |
| 2015/0186600 A1 * | 7/2015 | Diaz | ..................... | G06F 19/323 705/3 |

OTHER PUBLICATIONS

Quantin, Catherine, et al. "Medical record search engines, using pseudonymised patient identity: an alternative to centralised medical records." international journal of medical informatics 80.2 (2011): e6-e11.*

* cited by examiner

*Primary Examiner* — Mark Holcomb
(74) *Attorney, Agent, or Firm* — Gary K. Price

(57) ABSTRACT

An online system and software application and method for transmitting and transporting patient medical records at the discretion of the user between the user's personal health records cloud-based system and point of care physician for the express purpose of receiving medical consultation. Additionally, the system provides the ability to capture, retrieve, transport medical records from point of care physician for return to the cloud based personal records based system with automatic self-parsing and population into the user medical records system. The present invention provides total interoperability of patient medical records information between all present EHR/EMH electronic medical records based systems.

18 Claims, 6 Drawing Sheets

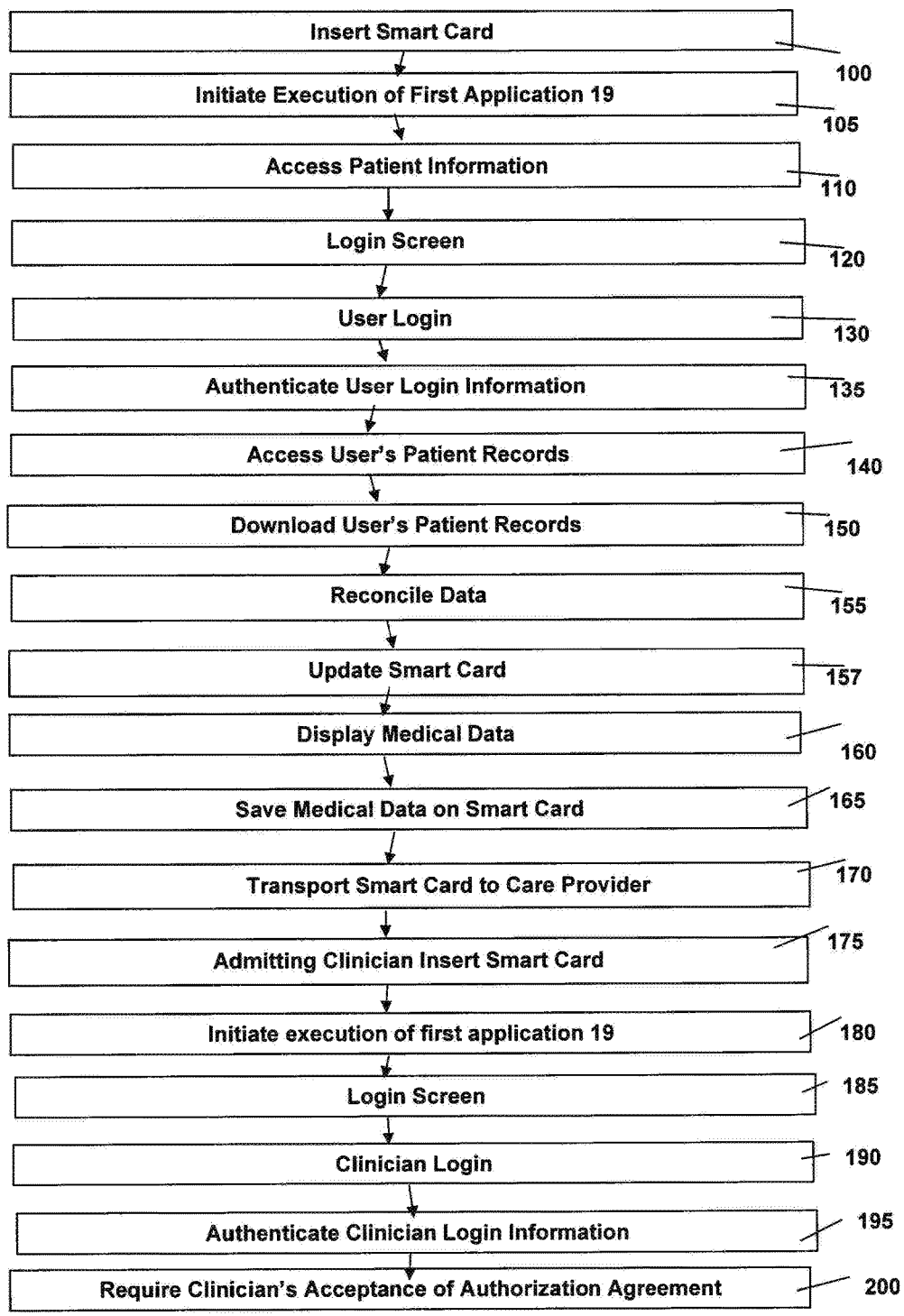

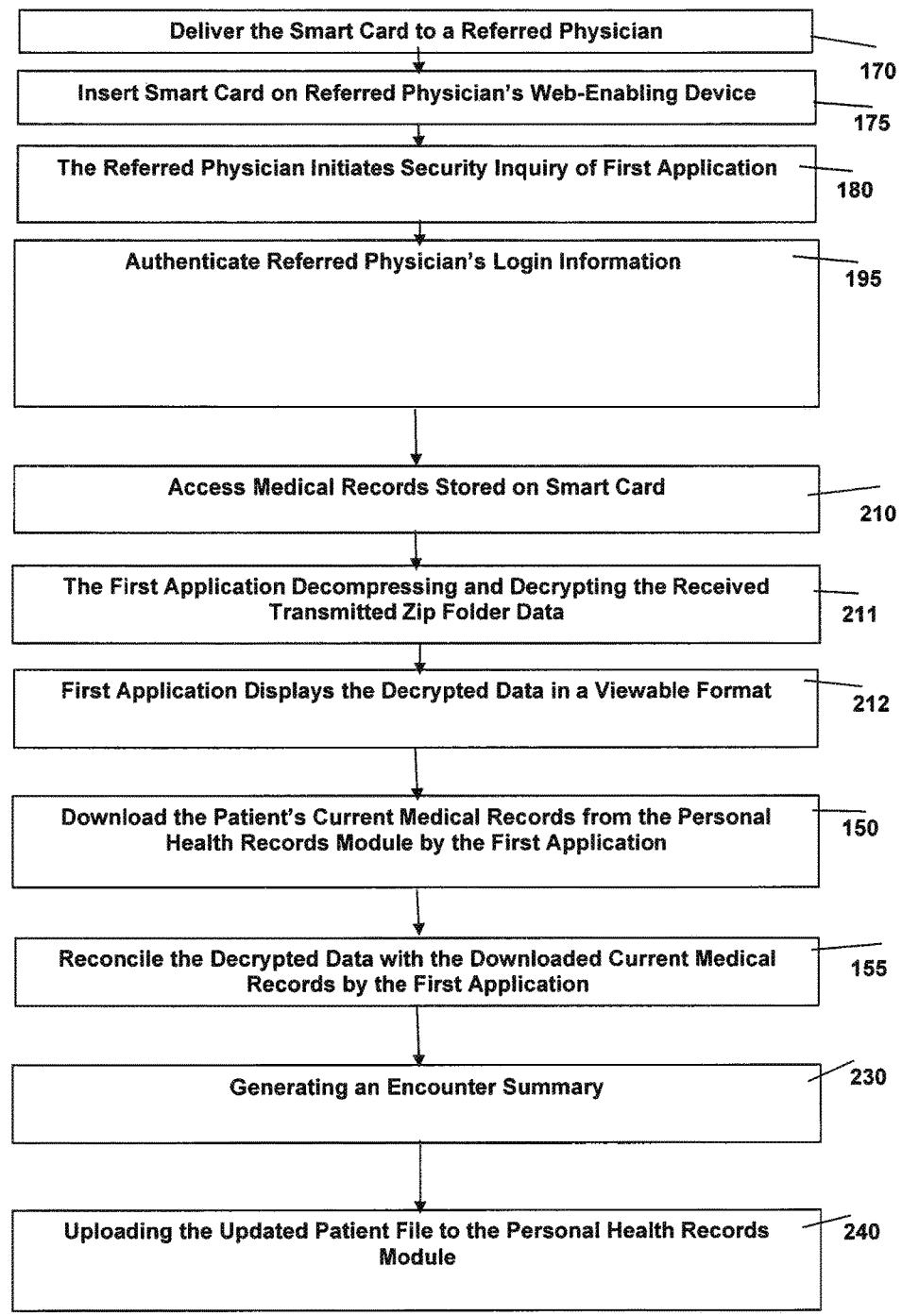

UNIVERSAL ACCESS SMART CARD FOR PERSONAL HEALTH RECORDS SYSTEM

CROSS REFERENCES TO RELATED APPLICATIONS

U.S. Provisional Application for Patent No. 62/022,912, filed Jul. 10, 2014, with title "Universal Access Smart Card PHR System" which is hereby incorporated by reference. Applicant claims priority pursuant to 35 U.S.C. Par, 119(e)(i).

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

The present disclosure relates to a system and method for capturing, storing, retrieving, and transmitting patient medical records, including longitudinal history and imaging throughout the healthcare system environment, and more particularly, to a system and method for communicating patient medical records that provides optimal medical information service to a subscribed recipient by managing an integrated medical information processing and transport system. The present invention provides total interoperability of patient medical records information between all present EHR/EMR electronic medical records base systems.

The present disclosure further provides for the ability and functionality to generate, capture and transmit a comprehensive set of medical information in compliance with CCD/CDA/C-CDA interoperability standards from a host health records system to a smart card for use in transport of same to a distant care provider, and the ability to open, view and download the data files in a manner that the data can be uploaded into a disparate system in use by the care provider in connection with providing medical services.

While other existing solutions are capable of copying medical files to a flash drive or similar storage device in a non-structured format, such process yields the stored data generally useless in being capable of being captured, uploaded and parsed into disparate electronic medical records based systems or in structured format. Due to the vast amount of data contained in a typical user's medical record, and using traditional methods for handling medical records, this has limited the application for electronically transferring medical records.

The present invention provides for the ability to upload data associated with any/all medical services provided by distant physicians and transport such data to the host system whereby the data is parsed into the host medical record as structured data.

2. Brief Description of Prior Art

Comprehensive medical care often requires a patient to visit more than just one doctor. While many patients have established a long-standing relationship with their primary care provider, they are generally unfamiliar with more specialized doctors until medical circumstances necessitate a referral to one. Upon receiving a referral, the patient is usually left to arrange an actual appointment with the specialist. However the patient usually relies upon the patient's primary care provider to timely forward the patient's relevant medical records to the specialist prior to the scheduled appointment. There is little transparency in this process, and under unfavorable circumstances a patient may find himself/herself referred to a doctor who has not been given access to the necessary medical information relating to that patient due to slow delivery, mistaken delivery, and/or failure to deliver. These hurdles may cause delays in medical care, and in some cases even dissuade patients from complying with their primary care provider's recommendation to seek additional medical care from a specialist.

Existing EHR/EMR (Electronic Health/Medical Records) systems do not always communicate with each other whereby patient information can be exchanged.

Other existing solutions in the prior art only copy medical files to a flash drive or similar storage device in a non-structured format which yields the data useless in being capable of being captured, uploaded and parsed into disparate medical records systems. Additionally, the medical files or data is generally in an unprotected state and susceptible to unauthorized access and use.

The problem does not end with the sharing of patient's medical records. There is no protocol for sharing of patient information between the primary and secondary care offices. The process requires someone to establish communications between one or more of the patient's primary care physicians and the secondary care physician(s). The inefficacies in managing this process are a drain on both the primary and secondary physician(s) offices. Often times, the patient, who has the least amount of medical knowledge and often an inability to anticipate or articulate the critical nature or timing of the referral, is left calling one or both offices and communicating with a receptionist who cannot independently determine what the next step in the process should be, without again involving either the primary or secondary care physician(s).

The issues described above have been long-standing problems for both physicians and patients, and substantially interfere with the ability to provide appropriate and cost effective medical care. Every existing electronic medical records based system known to applicant relies upon the health care institution and/or care provider to manage the patient's medical information independently.

The present invention provides total interoperability and portability of patient medical records information between all present EHR/EMR electronic medical records based systems. The present system manipulates the patient's updated medical records data to be sent to a referred physician into a format that can be retrieved and used in the referred physician's electronic medical records system with the ability to return data in the same specified format for integration back into the originating system database as structured data.

SUMMARY OF THE INVENTION

In one or more embodiments of the present invention, an apparatus and method are provided that manages the process of generating a complete and comprehensive set of patient medical records and the transport of said data to any physician for use in providing medical services to the patient with the ability to retrieve and transport all data related to the medical services provided by the physician back to their originating source.

In the preferred embodiment, a system and method is available for sharing by means of portability of patients' medical records throughout the continuum of care involving all care providers, either primary and secondary care providers and/or facilities. The present system allows various means of communications and medical records transfer between any health care practitioner practice groups, hospitals and other care provider locations. The system's servers provide a network-based service to the patient and all participating care providers, in order to allow the patient's medical records to be made available to transport to selected practitioner groups, hospitals and medical specialists, by providing a web-based data processing service and hardware interface to any medical provider.

The present invention provides for the ability and functionality to generate, a comprehensive set of medical information in compliance with C-CDA/CCR/CCD/CDA interoperability standards from a host electronic personal health records system to a smart card (common access card (CAC) or other relevant smart card known in the art) for use in transport of same to a distant care provider and the ability to open, view, and download said data files in a manner that said data can be uploaded into a disparate system and used by the care provider in connection with providing medical services. Additionally, the invention provides for the ability to upload data associated with any/all medical services provided by the distant physician and transport to the host system whereby the data is parsed into the host medical record as structured data.

The smart card is used as the storage device of a Health Information Exchange (HIE) module, and the transport of all patient data received from the originating source (personal health records module) to the distant care provider.

The personal health records module is the originating and ultimately the end receiving point of all patient medical information sent to the care provider and returned to the originating system. A user computer or other web-enabled device having an executable HIE application software program (referred to as the "first application") 19 serves as the host computer that provides web access to the cloud for connection and communication with the source patient personal health records module. And as mentioned, the HIE module (referred to as the "second application") 22 is embedded on the smart card and provides the logic and processing for storage and parsing of patient medical data. As will be understood, the smart card is mobile in nature, and can be updated from the point of care and cloud anywhere, at any time.

These new features bring significant benefits to patients, doctors and hospitals, increasing the efficiency of their work flows and improving patient care while reducing administrative costs, and the probability of errors in patient care.

DESCRIPTION OF THE PREFERRED EMBODIMENT

Figure 1:
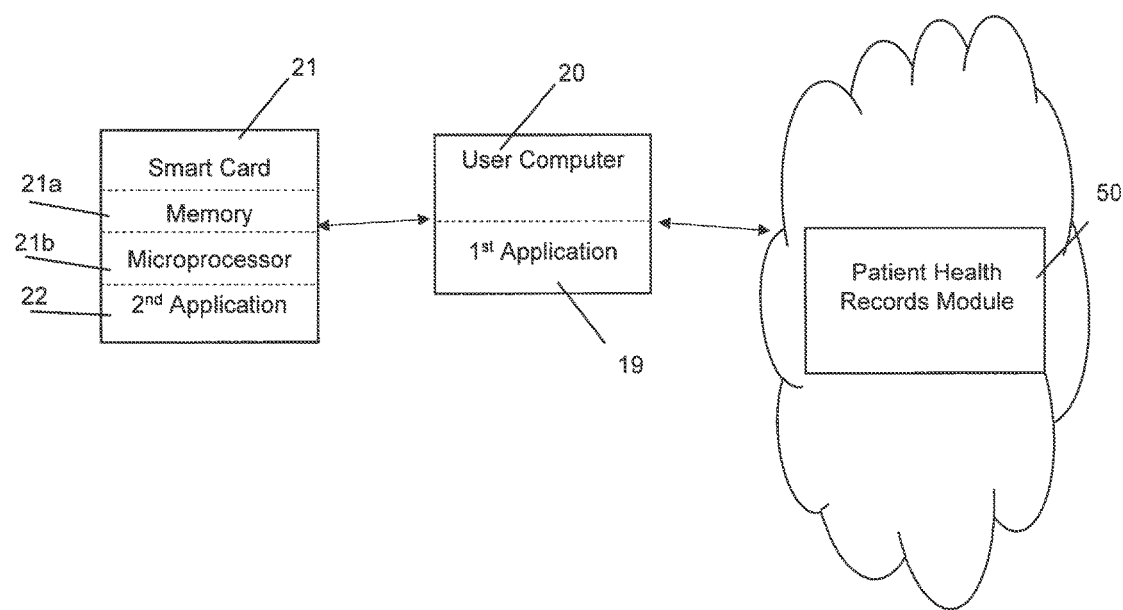
FIG. 1 is a schematic representation of the cloud service for implementing the present invention.
Figure 2:
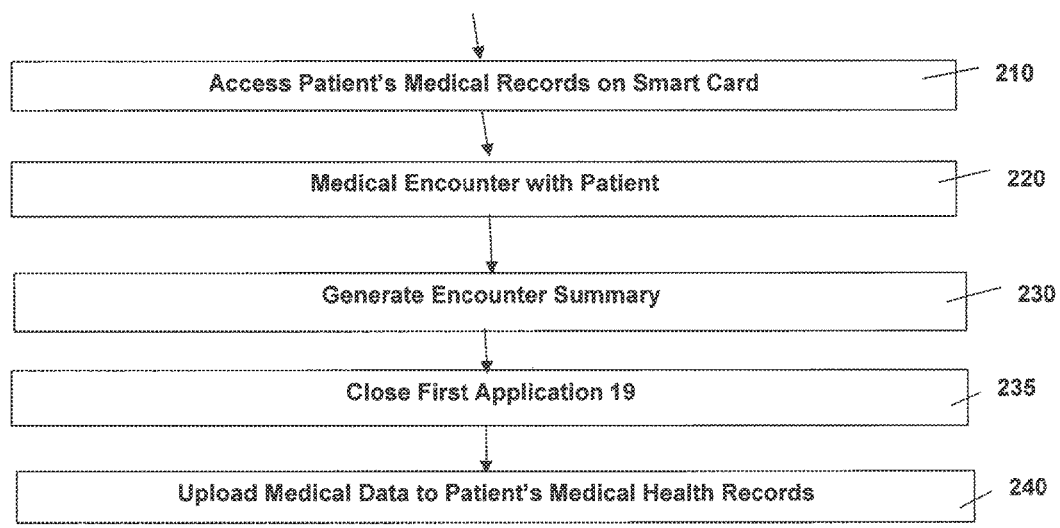
FIG. 2 is a flowchart of an exemplary application illustrating a method and apparatus for transmitting patient medical data to a remote health care provider.
Figure 3:
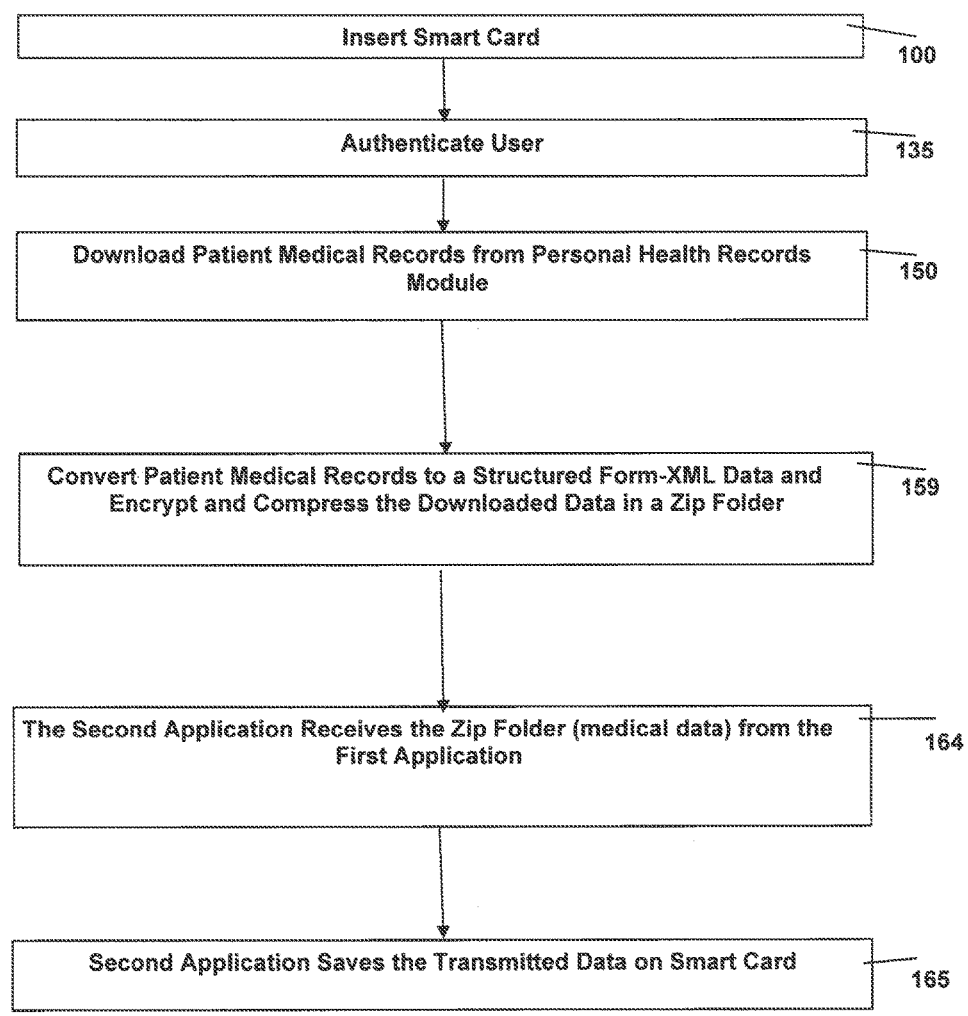
FIG. 3 is a flowchart of an exemplary application illustrating a method and apparatus for a client-side application of the present invention transferring medical data to a server-side application of the present invention.
Figure 4:
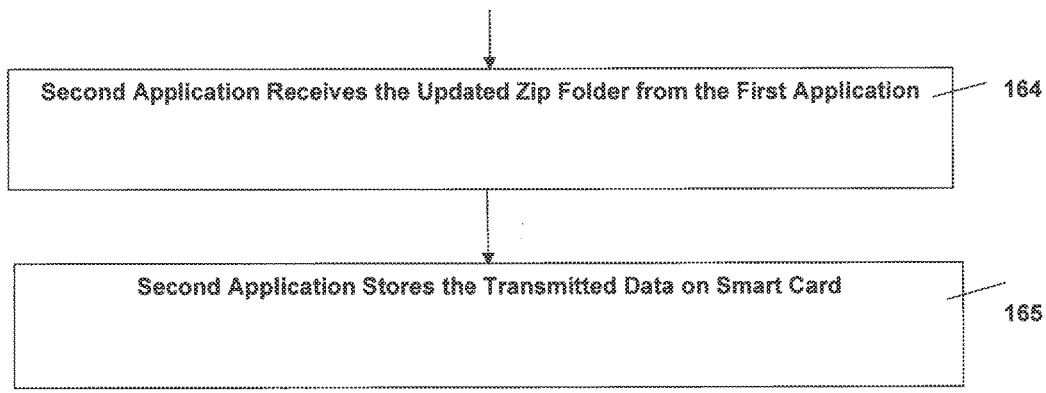
FIG. 4 is a flowchart of an exemplary application illustrating a method and apparatus for the server-side application of the present invention transmitting patient medical data to the client-side application of a referred physician.

In the preferred embodiment of the present invention, an apparatus and method is provided that manages the medical records data of a patient across the continuum of care involving multiple care providers or medical institutions for the purposes of receiving medical services involving, but not limited to, the process of physician referrals, whereby a patient is referred from one physician (primary care provider) to another physician (the referred-to or receiving physician or specialist) for a particular medical procedure, or analysis or care. Other existing solutions only copy medical files to a flash drive or similar storage device in a non-structured format which yields the data useless in being capable of being captured, uploaded and parsed into disparate electronic medical records based systems or in structured format. Due to the vast amounts of data contained in a typical user's medical record, and using traditional methods for handling medical records, this has, in the past, prohibited the application of transferring patient medical records. As will be described, the present system as disclosed eliminates this problem and consists of components configured and correlated with respect to each other so as to attain the desired objective.

The present disclosure builds on a previous disclosure of the Applicant relating to a software application that provides the logic from which to orchestrate the retrieval of records from a cloud-based personal records based system.

The present disclosure is in communication with the cloud-based personal records based system in order to receive data in a structured format, and packaged in a compressed state for handling and storage on small capacity smart cards (CAC or other) and with the logic as required to be capable of automatically unwrapping the compressed package of data in such a way as to be viewable, printable and downloadable in a format that is universally usable by any certified electronic health records based system in North America.

The present disclosure differs from what currently exists. The present invention uses NIST Standards from which to serve as a common format for which every certified EMR can communicate. Additionally, the present invention uses a common protocol for packaging the data in a compressed state that permits its use with small capacity circuit chips as those found in the smart cards.

Transfer of Patient Records

Over the course of a multi-doctor treatment process, a patient's medical records must often be transferred between several offices. Each of these transfers carries with it the possibility of document loss, and the frequent use of physical patient records (paper) only serves to increase this risk.

There is no widely used specialized procedure in place to efficiently facilitate transfer of records between healthcare providers either in private practices or Hospital-based physicians, meaning that a responsible patient and cooperative, well-organized practices must be present to ensure each doctor is properly informed. Three-way communication between the patient and multiple medical services locations is at best cumbersome, and at worst ineffective in ensuring that records are transferred completely and in a timely fashion. Breakdowns in communication and record transfers can lead to unnecessary procedures, inappropriate medication, preventable deaths, and superfluous testing that combine to create additional cost for patients and insurance providers, all the while eroding trust in medical providers and causing frustration on all sides.

The present invention is directed to a solution that provides for the capture, storage, retrieval and transmission of patients' medical records including longitudinal history and imaging (hereinafter "medical data") throughout the healthcare system environment. Application of a software program (referred to as the "first application") 19 executable from a user's web access computer as will be described, provides for the ability and functionality to generate, capture and transmit a comprehensive set of medical data in compliance with CCD/CDA/C-CDA interoperability standards (referred to as step 159 in drawings) from a cloud based personal health records module 50 to a smart card 21 for use in transport of same to a distant care provider and the ability to open and view, download the medical data (generally referred to as steps 210, 211 and 212) in a manner that the data can be uploaded into a disparate system in use by the care provider in connection with providing medical services. As such, the present system resolves problems associated with interoperability between existing and legacy health records systems by providing one central all-inclusive repository of patient medical data by way of a smart card, a user computer and a cloud-based personal health records software solution with the ability to generate a continuity of care document in a format as described above that is capable of being parsed into any disparate medical health records system and the ability to retrieve and receive a continuity of care document in such structured format as previously identified back to the central repository whereby the data is parsed back into the patient record based system.

In the preferred embodiment, the present disclosure includes a smart card 21 having a memory 21a and a microprocessor 21b for executing a Health Information Exchange ("HIE") application (the "second application") 22. The microprocessor 21b is a small capacity circuit chip available in smart cards for executing the second application 22 and for packaging of medical data in a compressed state that is stored on the smart card 21. The smart card 21 for transporting patient medical data from the originating source, the personal health records module 50 to the distant care provider 60. The Personal Health Records module 50 is the originating and ultimately the end receiving point of all patient medical data. A user computer 20 or other web enabled device provides web access to the cloud 25 for connecting and communicating with the source patient personal health records module 50. The second application 22 further provides the logic and processing to receive patient medical data, whereby the medical data is compressed for storage, or unwrapped for viewing, and parsed in a format that is useable by a disparate medical records system.

For purposes herein, reference to the user computer 20 shall refer to a personal computer or other web-enabled device that providers web access to the cloud 25, and having the first application 19 in executable form. Further, a general reference to user computer 20, may, when relevant, refer to the execution of the first application 19 on the user computer 20. Further, the user computer 20 refers to the user/patient's personal computer or the patient's care provider's computer.

The Personal Health Records module 50 serves as the central repository for all patient medical records. The Personal Health Records module 50 receives, stores, and transmits from, all patient medical data and records. All medical data is made available in structured form using the NIST standard for CCR, CCD, CDA or C-CDA for user by the end-user (physician) in downloading the data into their respective disparate operating system. As a result, the present invention has the ability to allow a user to append medical data of any known format to the CCR/C-CDA/CCD/CDA transfer document(s) for user by the physician in providing diagnosis.

As will be further understood, once the attending physician has access to the medical data, any electronic response from the physician following a medical encounter, such as the encounter summary including comments, suggestions and recommended orders by the attending physician (medications, tests, etc.) should be uploaded to the patient's cloud based personal health records 50 and retrieved from the personal health records module 50 and saved on the smart card 21 in the structured form, and the smart card 21 delivered to the user.

The first application 19 further defines a reconciliation process that is processed by the user's computer, whereby the data received/data stored on by the smart card is logically compared with the data in the personal health records module 50 to avoid duplication. The reconciliation process is both automatic and manual in that all data received is brought to a user webpage screen on the user computer 20 when the first application 19 is initiated and presented to the user with both existing data and newly received data so that the user can either accept or reject the inclusion (into the personal health records module) of the newly received data at the user's discretion.

In the preferred embodiment, the smart card 21 is configured to store the second application 22 on the smart card 21 in such a way that provides integrity of the second application 22 and the integrity and encryption of data within the second application.

It is critical to note that the use of the personal health records based system as discussed, is independent of the medical care provider's own electronic medical records system but yet capable of communicating with the provider's medical system or any other medical records based system. This is the founding principle of the present system that cannot be altered. The present system is therefore independently operated using a cloud system.

Relationship Between the System's Components

The second application 22, as disclosed, is embedded on the smart card 21 and can be run with the user's web-enabled personal computer 20.

The user computer 20 with smart card reader technology provides web access to the cloud for connection and communication with the source patient personal health records module 50. The cloud-based personal health records module 50 serves as the originating source of all patient medical data and ultimately the end receiving point of all patient medical data as uploaded by the care provider and returned to the originating system.

The smart card 21 is used for both authentication and as a portable means of storage for medical data involving personal information including longitudinal medical history information. As a storage vehicle, it provides a secure carrier for all patient data to and from the originating source to the distant care provider. Medical data stored to the smart card 21 is inaccessible without access to the first application 19, and without the required unique login information as will be discussed.

Domestic medical information processing technology includes Picture Archiving Communication System (PACS), Order Communication System (OCS), and Electronic Medical Record (EMR), which comply with Health Level 7 (HL7). Medical information processing is independently managed by individual hospitals. Particularly, EMR has been developed into the Electronic Health Record (EHR) concept that is a lifetime electronic health record of individual patients.

However, EHR independently operated need to be integrated according to standardization for high quality medical service of individuals. For this, integrated system technology is needed, and for example, a cloud computing model is being applied.

Cloud computing is a next generation computing technology in which Software as a Service (SaaS) for web 2.0 service and utility computing are complexly combined.

The service structure of cloud computing may include a server for using IT environment, storage, Infrastructure as a Service (IaaS), Platform as a Service for providing a basis for development of software, Software as a Service (SaaS) in which a computing provider supplies and uses software through Internet. The present system may further include mobile browser technology which is a software-manufacturing technology with an app structure used to independently provide developed services to a user in a smart environment.

Network Communications

As used herein, database is meant to include any of various types of data repositories and processes for indexing, searching, storage and retrieval from such repositories.

The personal health records module can further include a DICOM viewer module for viewing and processing "native" DICOM imaging from any source known.

Physicians and Practice Groups

In various embodiments of the present invention disclosed herein, the term "physicians", "care providers", "doctor" or "clinician" refers to a physician administering patient care, as well as to those members of his/her staff responsible for maintaining the physician's patient records. Though the term is used interchangeably, it should be understood that in the exemplary figures and texts, each function is being performed by one or more persons that perform such activities in a particular doctor's office on behalf of a licensed physician.

The term "specialist" is applied to a physician administering secondary care to a patient after a referral from a referring physician, and is also applied to other members of his/her staff in the same manner as is done for the physician. It may be possible for any given physician to in one situation be a specialist (receiving a patient via referral), and in another be a primary care physician (referring a patient to another physician for specialized care).

Further a "provider group" or "practice group" may be any entity linking a group of doctors through shared facilities, services, or referral agreements. This can include but should not be limited to integrated multi-facility hospitals, medical groups, and multi-doctor practices.

System, Method and Computer Program

As will be appreciated by one skilled in the art, the present invention may be embodied as an apparatus or method, including a computer system or computer program product. Accordingly, unless specified to the contrary, the present invention may take the form of an entirely hardware embodiment, and entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code stored in the medium.

Any combination of one or more computer-usable or computer-readable medium(s) may be utilized, unless specified to the contrary herein. The computer-usable or computer-readable medium may be, for example, but not limited to, electronic, magnetic, optical, electromagnetic, infrared, or semiconductor storage mediums. More specific examples (a non-exhaustive list) include: a portable computer diskette, a hard disc, a random access memory (RAM), a read-only memory (ROM), an erasable programmable read-only memory (EPROM or Flash Memory), and a portable compact disc read-only memory (CDROM), an optical storage device.

Further, the present invention is described above with reference to flowchart illustrations and/or block diagrams of methods, apparatus and computer program products (systems) according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams illustrate the architecture, functionality, and operation of possible implementations of systems, methods and computer program products according to various embodiments of the present invention. In this regard, each block in the flowchart or block diagrams may represent a module, segment, or portion of code, which comprise one or more executable instructions for implementing the specified logical function(s). It should also be noted that, in some alternative implementations, the functions noted in the block may occur out of the order noted in the figures. For example, two blocks shown in succession may in fact, be executed substantially concurrently, or the blocks may sometimes be executed in the reverse order, depending upon the functionality involved. It will also be noted that each block of the block diagrams and/or flowchart illustration, and combinations of blocks in a block diagrams and/or flowchart illustration, can be implemented by special purpose hardware-based systems that perform the specified functions or acts, or combinations of special purpose hardware and computer instructions.

Referring to the drawings, in application, the first and second applications 19, 22 serve as the initiator of all steps in the creation and processing of data compilation and dissemination of medical data between the originating source 50 and the receiving designation information system and the retrieval of information from the destination system and subsequent transport and dissemination back and into the originating information system.

The user/patient first inserts 100 the smart card into a user computer's 20 card reader or other like web-enabled device. The user's computer 20 initiates execution 105 of the first application 19 on the user's computer 20 that accesses 110 the patient's information contained on the smart card 21 and present a user login screen 120. The user is required to log into the system 130 with its unique username and password. The first application 19 authenticates 135 the user's login information against the patient data contained on the smart card 21, and the personal health records module 50 when Internet is available. Further when Internet access is available, the user's computer 20 will then navigate to the user's based central silo personal health records system 140 and download 150 all medical data in a C-CDA format. The first application 19 then reconciles 155 the patient's medical data retrieved from the module 50 against the data stored on the smart card 21 and updates 157 the smart card if appropriate. The medical data can then be displayed 160 on the user computer in a viewable and printable fashion. The second application 22 will then receive 164 the medical data and save 165 the medical data on the smart card 21 in the original NIST format suitable for use in importing to any certified records system as structured data or to be uploaded into any uncertified operating system. It should be understood that the medical data includes both structured and unstructured data files. These unstructured data files include any medical imaging, scanned documents, etc. for either viewing or downloading. Once the user/patient has successfully loaded the most recent copy of their medical records data to the smart card 21, they remove the smart card from the card reader for transport 170 to an admitting clinician.

The user will transport 170 and then present the smart card 21 to the admitting clinician for use in establishing identity, insurance, benefits and providing a longitudinal personal medical history of data for use by the clinician during the medical visit/encounter. The admitting clinician will insert 175 the smart card into their user computer 20 to launch 180 the first application 19. Upon loading the first application 19 into their web-enabled computer and inserting the smart card 21, the clinician is presented 185 with a user login screen and in the preferred embodiment, is asked 190 for the user/patient's username and to enter their NPI (National Provider Identifier). The first application 19 then authenticates 195 both the patient, the received smart card 21 and the admitting clinician against a national care provider database (NPI). Once the system authenticates the user/patient and clinician, in the preferred embodiment, the system displays a HIPAA Release and Authorization agreement for acceptance 200. Upon acceptance by the clinician by clicking the Accept box, the clinician is allowed access 210 to the patient's records stored on the smart card 21. As should be understood, upon access to the medical data on the smart card 21, the first application 19 will unzip 211 the folder which contains an XML file and an XSL file style sheet. The first application 19 will then load and display 212 an XML generated style sheet representative of a continuity of care document in a viewable, downloadable and printable format.

The care provider may now view all of the longitudinal medical data of the user/patient to include image files in native DICOM for use in providing medical services 220 to user/patient with the knowledge that they have all the patient's medical information at their immediate disposal. Additionally, the data as presented is in accordance with the NIST Standards and as such can be downloaded and parsed back into any medical records system. The data is also made available in such viewable and printable format as to be downloaded for storage and future use in any legacy operating system.

Upon completion of the medical encounter with patient, the admitting clinician will generate 230 the encounter summary that includes comments, suggestions and recommended orders by the attending physician. When closing 235 the first application 19, the clinician is asked if it would like to upload the available medical data. The clinician can choose to do so immediately or at a later time. If the clinician elects to upload immediately, the clinician is presented with a screen from which to select data files, designate what clinical category folder they are most associated with and upload 240 the medical data to the cloud-based personal health records 50. If the clinician elects to "wait" to upload the medical data, the data is saved on the clinician's computer to be uploaded to the patient's originating source (personal health records module) 50 at a later time.

As should be understood, it is important to the present system that the clinician timely upload medical data following a medical encounter so that the patient's files stored on the personal health records module 50 remains up to date. In the event the clinician elects to "wait" to upload the most recent patient's data files stored on the clinician's computer and ultimately fails to update the data 50, the present disclosure includes a verification module that provides verification of receipt of patient's medical records data from the attending physician. In application, when medical service claims are submitted by the admitting clinician for medical services rendered, the system can retrieve a viewable, printable and downloadable copy of the patient encounter records for direct reconciliation for services "received" against, the admitting clinician's medical claim/invoice for medical services provided. In the event the admitting clinician's medical service claims are not supported by patient data stored in the cloud-based patient medical records 50, i.e., the admitting clinician never uploaded the patient's medical records from the subject medical encounter, the admitting clinician's claim for services would be returned to the admitting clinician with a suitable notation to the effect that "the medical claim for services provided to the referenced insured/patient is being returned for the lack of patient's medical records as required by the subscriber in keeping with the newly developed patient medical records reconciliation program," Once the admitting clinician uploads the patient medical records, and resubmits its claim for medical services, and upon verification of the same, the admitting clinician's claim for medical services could be processed.

As should be understood, the smart card 21 will retain the most recent data file as was presented to the care provider. The next time the smart card is inserted into a user computer 20, the first application stored on the user computer 20 will synchronize with the host system as described and, if needed, download from the data 50 a more recent copy of the patient's medical records including the data as was provided by the last care provider.

Although the above description contains many specificities, these should not be construed as limiting the scope of the invention but as merely providing illustrations of some of the presently preferred embodiments of this invention. As such, it is to be understood that the present invention is not limited to the embodiments described above, but encompasses any and all embodiments within the scope of the claims.

I claim:

1. A multi-user data management system for transmitting, retrieval and further processing of patient medical records, comprising:
   a cloud system,
   a first application accessed via a user terminal configured to allow a user to use a medical information processing service and inducing access to the cloud system taking charge of medical information processing, said first application including a style sheet configured to process data extracted from a zip folder,
   a smart card having a memory and a microprocessor, said microprocessor configured to execute a second application stored on said smart card,
   a cloud-based personal health records software module, wherein said personal health records software module configured to receive and manage a patient's patient records and said first application configured to transmit said patient records to said second application to be stored on said smart card, and
   wherein said first application configured to upload said patient records from said user terminal to said cloud-based personal health records software module and further configured to retrieve said uploaded patient records to store on said smart card in a structured format configured to be parsed and imported into a referred physician's disparate medical health records system at a database level, and said first application further configured to encrypt and compress said encrypted data in said zip folder, and wherein said second application configured to receive said zip folder and patient's identity information from said first application and save in said memory to transport said smart card to a referred physician, and wherein said second application further configured to transmit said zip folder and patient's identity information to the first application, said first application further configured to unzip said zip folder and decrypt said unzipped data and display said decrypted patient records in a viewable format using said style sheet, said first application further including a verification software in communication with said second application, and wherein said verification software includes said second application configured to not allow said referred physician's disparate medical health records system access to said zip folder and said zip folder is therefore not transmitted to the first application for access by the referred physician until the referred physician completes a user login screen that prompts the referred physician for information including the patient's identity information and the referred physician's national provider identifier, and wherein said first application configured to authenticate the patient's identity information by electronically comparing the patient's identity information entered by the referred physician with the patient's identity saved in said memory and further configured to electronically compare the referred physician's national provider identifier against a national care provider database, and wherein said multi-user data management system including said first and second applications and said personal health records software module are independent of said referred physician's disparate medical health records system.

2. The system as recited in claim 1, wherein said first application further comprising an interface function of outputting, managing, and software processing an event generated by the cloud-based personal health records software module.

3. The system as recited in claim 2, wherein said patient's identity includes a patient's unique username and wherein said second application configured to transmit said patient's unique username to said first application and said first application further configured to electronically compare the patient's unique username with said security information submitted by the referred physician.

4. The system as recited in claim 2, further providing a function of said first application comparing a physician's identifier saved on the personal health records software module with the security information submitted by the referred physician.

5. The system as recited in claim 2, further enabling the referred physician to form a response and said first application uploading said response to said patient health records software module in said structured format.

6. The system as recited in claim 5, wherein said first application further including a reconciliation software module configured to compare said decrypted patient records received from the smart card with the patient records stored in the cloud-based personal health records software module.

7. The system as recited in claim 6, wherein said reconciliation software module is configured for said first application to transmit an up-to-date medical records file to the smart card when said user terminal is connected with said cloud system.

8. An online transfer of patient medical records apparatus comprising:
an initiator configured to disseminate a patient's medical records between an originating source and a distant care provider, said initiator including a memory and a microprocessor, said microprocessor configured to execute a second application stored on said initiator,
a web access to cloud device configured to connect and communicate with a cloud-based personal health records software module that is a central repository for all patient medical records, said web access to cloud device configured to communicate with said second application on said initiator, said web access to cloud device includes a first application configured to be utilized by the originating source to retrieve medical records from the cloud-based personal health records software module, and said first application further configured to compile said medical records in an XML format configured to be parsed for inclusion into a distant care provider's medical health records system, and encrypt and compress said XML data in a zip folder and transmit said zip folder and a unique identifier to said second application for storing on the initiator, and said second application configured to transmit said zip folder and the unique identifier to said first application and said first application further configured to unzip said zip folder and decrypt said unzipped XML data, and view said decrypted XML data by the distant care provider using a style sheet,
said first application further includes a reconciliation software module configured to compare the decrypted XML data with the medical records in the cloud-based personal health records software module, and
wherein said second application does not transmit said zip folder to said first application for said distant care provider's access until said first and second applications successfully complete a security verification, said security verification includes said first application prompting said distant care provider to enter the distant care provider's national provider indicator and said first application authenticates said national provider identifier with a national care provider database and further includes authenticating the patient's unique identifier stored on said initiator, and wherein said first and second applications and said cloud-based personal health records software module are independent of said distant care provider's medical health records system.

9. The apparatus as recited in claim 8, wherein the initiator is a data storage device.

10. The apparatus as recited in claim 9, wherein said web access to cloud device is a user computer.

11. The apparatus as recited in claim 10, wherein the originating source is a patient.

12. The apparatus as recited in claim 10, wherein the originating source is a medical care provider.

13. The apparatus as recited in claim 10, wherein said storage device is a smart card.

14. A method for transferring patient medical records comprising the steps of:
inserting an initiator in a web enabling device, said initiator having a second application;
executing a first application in the web enabling device's processor, accessing through the first application a cloud-based personal health records software module, said first application configured to provide a web access to a cloud device to connect and communicate with said cloud-based personal health records software module, and downloading a patient's patient data from said cloud-based personal health records software module and, converting said downloaded patient data to a structured format configured to be parsed and imported into a referred physician's disparate medical health records system, wherein said structured format is an XML format, and encrypting and compressing said XML data in a zip file, and transmitting said zip file and a patient's unique identity to said second application, said second application configured to receive and store said transmitted data in a memory on said initiator; and delivering said initiator to a referred physician;

the referred physician performing the following steps:

connecting the initiator to the referred physician's web enabling device, said physician's web enabling device configured to execute said first application;

responding to a security inquiry from said physician's web enabling device, said security inquiry including said first application prompting said referred physician for information including the patient's identity information and the referred physician's national provider identifier and said first application authenticating the patient's identity information by electronically comparing the patient's identity information entered by the referred physician with the patient's unique identity stored in said memory and further electronically comparing said entered national provider identifier against a national care provider database, said second application transmitting said transmitted data stored in said memory to said first application, and wherein said transmitting said transmitted data step is not performed until said authentications of said patient's unique identity and said national provider identifier are successfully completed;

decompressing and then decrypting the transmitted data by said first application;

said first application displaying said decrypted data in a viewable format on said web-enabling device using a style sheet included with said transmitted data, on said first application, said viewable format representative of a continuity of care document;

executing said first application to access the cloud-based personal health records software module to reconcile the data stored on the smart card against the data in the cloud-based personal health records software module;

creating a reconciled patient file;

recording the referred physician's recommendations from the physician's web enabling device, and creating an updated patient file by including said physician's recommendations with the reconciled patient file, and converting through the first application said updated patient file to an updated XML data file and encrypting and compressing said updated XML data file by said first application in an updated zip folder, and said first application configured to transmit said updated zip folder to said initiator;

receiving said updated zip folder by said second application and said second application storing said updated zip folder in said memory; and delivering said initiator to said user.

15. The method as recited in claim 14, wherein the step of recording the referred physician's recommendations includes the step of saving said referred physician's recommendations on the physician's web enabling device and waiting a selected period of time before executing the creating an updated patient file step.

16. The method as recited in claim 15, further including the step of said first application merging said updated XML data file in said updated zip folder with said cloud-based personal health records software module and monitoring whether the referred physician completed the merging said updated XML data file step.

17. The method as recited in claim 16, including the step of denying the referred physician's medical claim for payment of medical services when said monitoring step shows the referred physician failed to merge said updated XML data file with said cloud-based personal health records software module.

18. The method as recited in claim 17, wherein said initiator is a smart card.

* * * * *